United States Patent

Novak et al.

[11] Patent Number: 6,059,782
[45] Date of Patent: May 9, 2000

[54] BIPOLAR HIGH-FREQUENCY SURGICAL INSTRUMENT

[75] Inventors: Pavel Novak, Schaffhausen, Switzerland; Arnaud Wattiez, Clermont-Ferrand, France

[73] Assignee: Storz Endoskop GmbH, Switzerland

[21] Appl. No.: 09/077,220

[22] PCT Filed: Nov. 20, 1996

[86] PCT No.: PCT/DE96/02214

§ 371 Date: May 20, 1998

§ 102(e) Date: May 20, 1998

[87] PCT Pub. No.: WO97/18766

PCT Pub. Date: May 29, 1997

[30] Foreign Application Priority Data

Nov. 20, 1995 [DE] Germany ............... 195 43 258

[51] Int. Cl.[7] .................................................. A61B 18/18
[52] U.S. Cl. ................................................ 606/48; 606/51
[58] Field of Search ........................ 606/41–42, 48–52, 606/36, 43, 46, 206, 207

[56] References Cited

U.S. PATENT DOCUMENTS

| | | |
|---|---|---|
| 4,261,630 | 4/1981 | Perez . |
| 4,567,890 | 2/1986 | Ohta et al. . |
| 5,178,606 | 1/1993 | Ognier et al. . |
| 5,383,876 | 1/1995 | Nardella ............................ 606/49 |
| 5,403,311 | 4/1995 | Abele et al. ...................... 606/49 |
| 5,445,638 | 8/1995 | Rydell et al. ..................... 606/51 |
| 5,562,720 | 10/1996 | Stern et al. ...................... 607/98 |
| 5,797,941 | 8/1998 | Schulze et al. ................. 606/171 |

FOREIGN PATENT DOCUMENTS

| | | |
|---|---|---|
| 536440A | 4/1993 | Germany ............... A61B 17/39 |
| 4417189A1 | 11/1995 | Germany . |
| WO 93/22979 | 11/1993 | WIPO . |

*Primary Examiner*—Linda C. M. Dvorak
*Assistant Examiner*—Roy Gibson
*Attorney, Agent, or Firm*—St. Onge Steward Johnston & Reens LLC

[57] ABSTRACT

The invention concerns a high-frequency surgical instrument comprising two electrodes which are designed as forceps jaws and to which a high-frequency current from a high-frequency generator can be applied such that a high-frequency current flows between the jaws through the area of tissue to be treated. The instrument according to the invention is characterized in that, for alternative cutting and coagulation, an electrically non-conductive spacer is provided which is introduced between the electrodes when tissue is being cut. At least one duct is provided for flushing and/or removal purposes.

27 Claims, 1 Drawing Sheet

BIPOLAR HIGH-FREQUENCY SURGICAL INSTRUMENT

DESCRIPTION

1. Technical Field

The present invention relates to a high frequency surgical instrument.

High-frequency surgical instruments of this type are utilized, in particular, as bipolar instruments.

2. State of the Art

To cut or coagulate tissue using high-frequency currents, whose frequency lies by way of illustration in the range between 500 kHz and 1 MHz, is known. Fundamentally one differentiates between monopolar and bipolar types of operation:

In monopolar operation, the current flows between one large area neutral electrode and a small operation electrode, also called an active electrode. The active electrode can, in particular, have the shape of a pointed tip or a small ball. Due to the high current density at the tip of the active electrode, only the tissue in the vicinity of this tip desiccates or burns, with cutting results or intensified coagulation occurring corresponding to the current shape (sinus, sinus with interruptions respectively impulse shape).

In bipolar operation, the flow of current occurs between two small electrodes enclosing a piece of tissue. In the past, this type of operation has been used for coagulation and in practice only to a small extent for cutting.

Contrary to bipolar operation, in monopolar operation, the current flows through large areas of the human body. Thus there is a danger that, particularly if not applied 100% properly, not only the tissue in the immediate vicinity of the active electrode is influenced in the desired manner by the flow of current, but by way of illustration a disturbance in heart function may occur due to a flow of current in the vicinity of the heart. Moreover, coagulation may also occur in tissue fibers, etc. which are located quite far from the actual coagulating site.

For this reason, for some time attempts have been made to obtain results even in bipolar type operation.

By way of illustration, the use of a "triode" is known in which the shape of the two electrodes of which the one is a pointed tip and the other a hemisphere, the conditions under which the monopolar type of operation are copied. On the basis of this form, cutting results are obtained only at the tip of the electrodes so that cutting is very precise. This shape of the electrodes however does not permit gripping the tissue to be cut.

A bipolar coagulation pair of tongs is known from German utility patent 92 15 590. These coagulation tongs are provided with two electrodes which are designed as the jaws of the tongs and therefore can serve as clamping electrodes between which the tissue to be cut is held respectively clamped. Tissue coagulation is performed by applying a HF current from a HF generator.

These known bipolar coagulation tongs are solely suited for coagulating tissue, however not for cutting it. Moreover, these coagulation tongs possess no channel which could serve as a rinsing and/or vacuum off channel by means of which, by way of illustration pieces of tissue could be vacuumed off.

Another bipolar coagulation pair of tongs are known from EP 0 589 453 A2. These bipolar coagulation tongs. Too. are neither suited for cutting tissue nor possess a channel which could be used for rinsing or vacuuming off.

The same applies to the bipolar tongs respectively instruments known from U.S. Pat. Nos. 5,269,782, 5,282,799, 5,258,006 and 5,290,285 as well as EP-A-0 596 436.

Another bipolar coagulation instrument is known from EP 0536 440. Although this instrument for high-frequency surgery is suited selectively for cutting or coagulating, it possesses neither a rinsing and/or vacuuming-off channel nor is it of optimum design for both types of operation.

Therefore the bipolar arrangement described in the printed publications mentioned in the preceding, to which, moreover, explicitly reference is made for the explanation of all details not explained more closely herein, have the disadvantage that they possess no rinsing and/or vacuuming-off channel. Furthermore, these bipolar electrodes cannot be employed in combination with conventional high-frequency surgical instruments like those already existing in conjunction with endoscopic systems already found in many physicians offices respectively clinics. Moreover, they either are suited only for coagulation and not for cutting or performance of one of the two functions, usually the cutting function, is not optimum.

DESCRIPTION OF THE INVENTION

The object of the present invention is to provide a high-frequency surgical instrument having two electrodes, which is especially suited for bipolar applications and optimally suited for "coagulating" type operation as well as for "cutting operation" and into which at least one channel, which can serve as a rinsing and/or vacuuming-off channel, is integrated.

An invented solution to this object is set forth herein.

The preferred embodiment is provided with an electrically non-conductive spacer which is inserted between the electrodes, i.e. between the jaws of the tongs. Furthermore, at least one channel is provided which serves as a rinsing and/or vacuuming-off channel.

Due to the electrically non-conductive spacer provided according to the present invention, when cutting the jaws of the tongs are spaced a minimum distance apart and therefore simultaneously (usually) an exactly defined distance, which can typically be 1 mm (claim 10) so that when the HF current is applied with a suited, known from the state of the art, wave form, optimum cutting results are obtained.

The channel provided according to the present invention can be formed in that the jaw holder encloses at least one channel which can serve as a rinsing and/or vacuuming-off channel. As an alternative, the channel can also be formed in that, in an as such known manner, jaws of the tongs run in an external tube, which encloses the rinsing and/or vacuuming-off channel. Of course, the rinsing channel and the vacuuming-off channel can also be provided separate: thus, one of the two channels can be enclosed by the jaw holders and the other channel is a concentric channel, which is bordered by the external tube.

In the improvement described herein, the jaws of the tongs, which serve as electrodes, end in a pointed tip, which not only facilitates gripping and holding the tissue but also ensures a defined flow of current, which preferably comes from the tips.

Particularly preferred is that the jaws are less wide in the region before the tip than in the region further back.

The tip may be disposed in the direction of the longitudinal axis of the instrument. However, particularly preferred is if the tip forms an angle with the longitudinal axis of the instrument, which by way of illustration can be 30°, preferably 90°, 120° or on the other hand preferably 180°. The jaws are replaceable so that jaws with different angles between the tips and the longitudinal axis of the instrument can be inserted in an instrument. In this manner a "basic instrument" can be optimally adapted to the respective surgery conditions.

A 90° offset tip has the advantage that it permits gripping the tissue in a simple manner.

If the tip is bent 180°, it is furthermore preferred if the tips lie within the contour of the jaws. In this manner, on the one hand, the tissue can be gripped securely and, on the other hand, a defined flow of current especially suited for cutting is ensured.

The spacer is preferably provided according to the present invention according to claim 8 as a slide which is actuated for cutting the tissue in such a manner that it is moved forward between the jaws so that the jaws are spaced a minimum distance apart. Furthermore, the spacer designed as a slide can be provided with a front edge so that it can be employed for mechanical cutting of tissue. Thus, it is preferred if it is designed in such a manner that it can be moved over the distal end of the electrodes respectively jaws.

The invented instrument can have a basic design similar to that of known instruments so that it can be utilized with existing instruments from a endoscope system, by way of illustration already existing trocar shafts or already existing endoscopes.

In particular, the jaws can be composed of a cambered elastic material so that they are open in the "normal state" and are closed by means of a relative movement between jaws and external tube as, by way of illustration, described in EP-A 0598 453. It is preferable if, as also described in this printed publication, that in order to close the jaws they are not drawn back but rather the external tube is moved forward, because the jaws do not have to be moved for closing the jaws, which under given circumstances could lead to the desired tissue section not being coagulated respectively cut.

In this embodiment of the tongs, it is furthermore preferred if the jaws are composed of a super elastic material and, in particular, a shape-memory material.

Alternatively, the tongs utilized according to the present invention can also be designed in such a manner that the jaws are joined at least to a joint and are actuated via (at least) one push or pull rod.

In any event, it is advantageous that the jaw holders also serve as supply lines for the jaws serving as electrodes and are electrically insulated from the surroundings.

The invented instrument can be utilized, by way of illustration inserted in a trocar shaft, for bipolar treatment and, in particular, for coagulating or cutting tissue in endoscopic surgery, but not solely therefor. Furthermore, the instrument is also suited for monopolar treatment. In this case, it is preferred if a combined connection to the monopolar and the bipolar output of a (known) high-frequency generator is provided.

In any event, the invented instrument is especially suited as a multifunctional instrument for bipolar cutting, monopolar or bipolar coagulating, for gripping or rinsing and, if need be, for cutting using the cutting edge of the slide.

For this purpose, the instrument can be composed of an, as such known, tong component as is known in endoscopic surgical instruments and an, as such known, multifunction handle with which the individual functions are controlled. Corresponding tong components and multifunction handles are produced, by way of illustration, by Karl Storz GmbH & Co., Tuttlingen, Germany.

In the alternative described herein, a high-frequency surgical instrument, as is known from EP-A 0536 440, is designed in such a manner that the tube-designed holder of the ring-shaped electrodes and the rod-designed holder of the pointed electrodes enclose a channel which serves as a rinsing and/or vacuuming-off channel. In order to optimize the "cutting type operation" the rod-designed holder of the pointed electrodes can be moved parallel to the longitudinal axis of the instrument so that always the optimum distance between the ring-shaped electrode and the pointed electrodes can be set.

Moreover, this invented design permits drawing the tip behind the ring-shaped electrode in such a manner that there is a minimum risk of injury when the instrument in inserted.

This second preferred embodiment of the invented instrument can also be provided with a combined connection to the monopolar and the bipolar output of the high-frequency generator.

In this preferred embodiment, the electrode holders can serve as supply lines for the electrodes. For this purpose, they are electrically insulated from the surrounding.

In a normal state, the ring-shaped electrode is disposed in the longitudinal direction of the instrument behind the pointed electrodes, whereas the distance of the ring-shaped electrode from the pointed electrode in the direction of the longitudinal axis is smaller or at most the same as the diameter of the ring-shaped electrode.

BRIEF DESCRIPTION OF THE DRAWINGS

The present invention is made more apparent in the following using preferred embodiments with reference to the drawing, in which.

DESCRIPTION OF PREFERRED EMBODIMENTS

Figure 1:
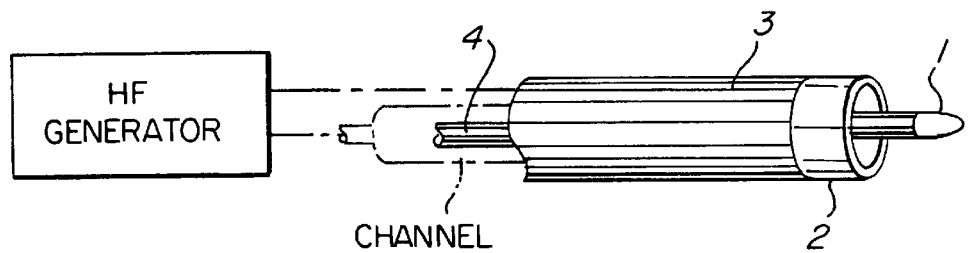
FIG. 1 shows a first preferred embodiment of the present invention.

FIG. 1 shows the distal end region of an otherwise not depicted bipolar high-frequency surgical instrument having two electrodes 1 and 2. The HF-surgical instrument may be designed in an, as such, known manner thus obviating a more detailed description here. In particular, the instrument can be a known HF instrument, such as by way of illustration manufactured in serial production by Karl Storz GmbH & Co.

Electrode 1 has the shape of a pointed tip and serves as a cutting electrode. Electrode 2 has the shape of a ring. Electrode 1 is held by a holder 4, which is designed as a rod, whereas electrode 2 is held by a tube 3. Rod 4 and tube 3 enclose a channel which can serve as a rinsing and/or vacuuming-off channel.

The electrode holders 3 and 4 also serve as supply lines for the electrodes from the proximally disposed connection for a not depicted HF generator and are electrically insulated from the surroundings.

The ring-shaped electrode 2 is disposed behind the pointed electrode 1 in the direction of the longitudinal axis of the instrument, with the distance of the ring-shaped electrode 2 from the pointed electrode 1 being smaller in the direction of the longitudinal axis or at most the same as the diameter of the ring-shaped electrode 2.

In a preferred embodiment, the pointed electrode 1 can be moved in relation to the ring-shaped electrode 2 in the direction of the longitudinal axis of the instrument, i.e. in the direction of the rod 4 and, in particular, can be drawn back "behind" the distal "end surface" of electrode 2.

The provision of a channel which permits rinsing and/or vacuuming off has, in addition to the ergonomic advantages due to the combination of HF cutting and rinsing instrument, also the advantage that simultaneous rinsing during cutting minimizes damage to the tissue and the cut particles can be quickly removed out of the body.

The bipolar electrode depicted in FIG. 1 is preferably designed for cutting.

Two preferred embodiments of the present invention, which can be utilized equally for cutting and bipolar coagulation, are depicted in FIG. 2.

The high-frequency surgical instrument depicted in FIG. 2 has the form of a pair of tongs, with the electrodes 1' and 1" being designed as the jaws of this pair of tongs. The actual tongs may be designed, by way of illustration, similar to known bipolar HF-tongs from Karl Storz GmbH &Co, Tuttlingen, Germany or in a manner as described, by way of illustration, in RP 0 589 453 A2. Of course, any other known HF tong design can also be employed.

In the two preferred embodiments depicted in FIG. 2, a pair of tongs are preferably employed in which the jaws 1' and 1" are composed of a cambered elastic material. Furthermore, the tongs are provided with an, also not depicted, external tube which receives the holders of the jaws 1' and 1" and other, described more closely in the following, parts of the tongs. By a relative movement between jaws 1' and 1" and the external tube, the jaws are drawn into the external tube and thus closed. It is preferred if for closing the jaws, the external tube is moved forward, because in this design the tong jaws gripping the tissue do not have to be moved in order to close the jaws. In particular, the jaws can be composed of a super elastic material, such as a shape-memory material.

Furthermore, it is preferred if the jaw holders enclose at least one channel which serves as a rinsing and/or vacuuming-off channel. If need be, another channel can be provided which is provided between the jaw holders and the not depicted external tube.

With the invented tongs, surgery can be performed, by way of illustration, as follows:

First, by way of illustration, access is created to the corporal cavity to be treated using a trocar having an inserted trocar thorn. Alternatively, a "natural" access can also be used.

Then, through the trocar (also referred to as trocar shaft), if need be under observation with an endoscope, an invented instrument can be inserted into the corporal cavity. The tissue section to be coagulated or cut is gripped by the electrodes 1' and 1" which are designed as tong jaws. "Moving" the external tube "forward", closes the jaws and fixes the tissue. Now the HF current from a not depicted high-frequency generator is applied to the two electrodes so that the tissue is cut or, depending on the temporal course of the current, coagulated.

Cut and not fixed parts of tissue can be vacuumed off through the channel provided according to the present invention.

Figure 2A:
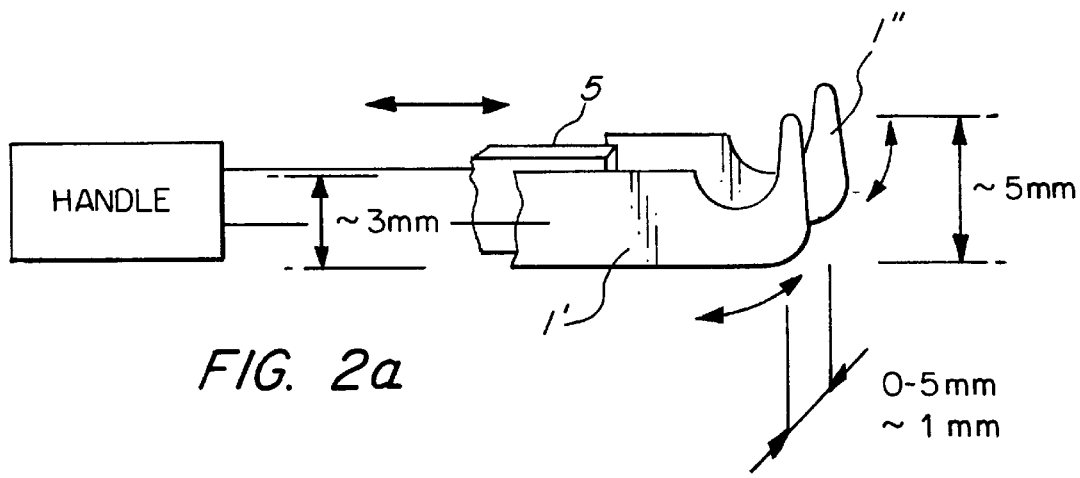
FIGS. 2a and b show alternatives of a second preferred embodiment of the present invention.
Figure 2B:
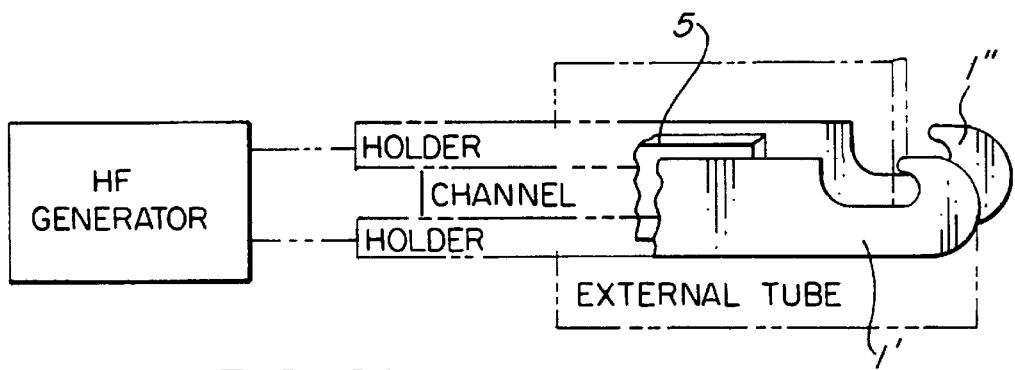

In the two preferred embodiments depicted in FIGS. 2a and 2b the two electrodes end in a pointed tip which forms an angle with the longitudinal axis of the instrument. In the embodiment depicted in FIG. 2a, the angle is 90°, whereas in the embodiment in FIG. 2b it is 180°. This, in particular if the jaws are replaceable so that jaws with different tip angles can be utilized, permits optimum adaptation to the respective treatment case. Explicit reference is made to the dimensions given in FIG. 2a, which are preferred for the invented design.

As the distance between the two electrodes, if the cutting results are to be selectively achieved, is critical, an electrically non-conductive spacer 5, which sets the distance between the electrodes 1' and 1" at approximately 1 mm when cutting, can be introduced through the channel provided between the electrodes. If coagulation is to be performed, the spacer is removed so that the distance between the electrodes can usually be set between practically 0 and 5 mm.

In order to improve the cutting results, the two electrodes are designed in such a manner that they are less wide in the region before the tip than in the back region, which advantageously influences the flow of current.

The holders of jaws 1' and 1", which are not shown in more detail, serve a supply lines for the jaws and are electrically insulated from the surroundings so that they can conduct the HF current from the not depicted HF connection to the distal end.

Alternatively, the jaws can be joined to at least one joint and actuated via a push or pull rod.

Furthermore, a cutting edge for cutting the tissue can be provided at the distal end of slide 5. Moreover, the instrument can be provided with a combined connection with the monopolar and with the bipolar output of the high-frequency generator.

What is claimed is:

1. A surgical instrument extending along a longitudinal axis and having two electrodes which have pointed tips extending at an angle with respect to the longitudinal axis and which are designed as the jaws of a pair of tongs, and which are adapted for application of a HF current from a HF generator, so as the HF current flows between said jaws through a tissue to be treated, an electrically non-conductive spacer is introduced between electrodes when cutting, and at least one channel is provided together with the tongs which serves a function selected from the group comprising rinsing, vacuuming and combinations of these, the jaws being replaceable, so that jaws having different angles can be utilized.

2. An instrument according to claim 1, characterized by the fact that said electrodes are less wide in a front region before said tip than in a back region spaced axially apart from the front region.

3. An instrument according to claim 1,
characterized by the fact that the angle is selected from the group comprising 0°, 30°, 90°, 120° and 180°.

4. An instrument according to claim 3,
characterized by the fact that said tip is a 180° tip and lies within the contour of said jaws.

5. An instrument according to claim 1, characterized by the fact that a distance between said electrodes is approximately 1 mm when cutting.

6. An instrument according to claim 1, characterized by the fact that said jaws are connected to electrically insulated holders.

7. An instrument according to claim 1, characterized by the fact that said instrument is provided with a combined connection to a monopolar and a bipolar output of a high-frequency generator.

8. A surgical instrument having two electrodes which are designed as the jaws of a pair of tongs, and which are adapted for application of a HF current from a HF generator, so as the HF current flows between said jaws through a tissue to be treated, an electrically non-conductive spacer is introduced between the electrodes when cutting, and at least one channel is provided together with the tongs which serves a function selected from the group comprising rinsing, vacuuming or combinations of these, said spacer being slidable relative to said jaws.

9. An instrument according to claim 8,
characterized by the fact that said spacer is provided with a cutting edge.

10. A surgical instrument having two electrodes which are designed as the jaws of a pair of tongs, and which are adapted for application of a HF current from a HF generator, so as the HF current flows between said jaws through a tissue to be treated, an electrically non-conductive spacer is introduced between the electrodes when cutting, at least one channel is provided together with the tongs which serves a function selected from the group comprising rinsing, vacuuming or combinations of these, and holders provided for mounting said jaws together with said channel and for enclosing said channel.

11. A surgical instrument having two electrodes which are designed as the jaws of a pair of tongs, and which are adapted for application of a HF current from a HF generator, so as the HF current flows between said jaws through a tissue to be treated, an electrically non-conductive spacer is introduced between the electrodes when cutting, at least one channel is provided together with the tongs which serves a function selected from the group comprising rinsing, vacuuming or combinations of these, and an external tube receiving said jaws.

12. An instrument according to claim 11,
characterized by the fact that said channel is provided in said external tube.

13. An instrument according to claim 11,
characterized by the fact that said jaws are composed of an elastic material and are closed by a relative movement between said jaws and said external tube.

14. An instrument according to claim 13,
characterized by the fact that for closing said jaws said external tube is moved forward.

15. A surgical instrument having two electrodes which are designed as the jaws of a pair of tongs, and which are adapted for application of a HF current from a HF generator, so as the HF current flows between said jaws through a tissue to be treated, an electrically non-conductive spacer is introduced between the electrodes when cutting, at least one channel is provided together with the tongs which serves a function selected from the group comprising rinsing, vacuuming or combinations of these, said jaws being composed of a super elastic material.

16. An instrument according to claim 15,
characterized by the fact that the material is a "shape memory material".

17. A surgical instrument having two electrodes which are designed as the jaws of a pair of tongs, and which are adapted for application of a HF current from a HF generator, so as the HF current flows between said jaws through a tissue to be treated, an electrically non-conductive spacer is introduced between the electrodes when cutting, at least one channel is provided together with the tongs which serves a function selected from the group comprising rinsing, vacuuming or combinations of these, said jaws being joined to at least one joint.

18. A surgical instrument having two electrodes which are designed as the jaws of a pair of tongs, and which are adapted for application of a HF current from a HF generator, so as the HF current flows between said jaws through a tissue to be treated, an electrically non-conductive spacer is introduced between the electrodes when cutting, at least one channel is provided together with the tongs which serves a function characterized by the fact that said instrument has a function selected from the group consisting of: bipolar cutting, monopolar coagulating, bipolar coagulating, gripping, rinsing, cutting and combinations of these and a multifunction handle connected to said jaws.

19. An instrument according to claim 18,
characterized by the fact that said instrument is provided with a multifunction handle.

20. A surgical instrument having two electrodes one of which has a pointed tip and the other of which forms a ring surrounding said tip, as a HF current is applied to the two electrodes in such a manner that it flows between the pointed tip and the ring through a tissue to be treated, a tube-designed holder for receiving said ring-shaped electrode, a rod-designed holder for receiving said pointed tip electrode, said rod-designed holder being movable parallel to a longitudinal axis of the instrument to uniformly cut tissue, and an electrically non-conductive spacer slidable between and relative to the electrodes when cutting.

21. An instrument according to claim 20,
characterized by the fact that said tip can be drawn back behind said ring-shaped electrode.

22. An instrument according to claim 20,
characterized by the fact that said instrument is provided with a combined connection to a monopolar and a bipolar output of a high-frequency generator.

23. An instrument according to claim 20, characterized by the fact that said electrode holders are electrically insulated from the surroundings.

24. An instrument according to claim 20, characterized by the fact that said ring-shaped electrode in a normal state is disposed behind said pointed tip electrode in a direction of the longitudinal axis of the instrument.

25. An instrument according to claim 24,
characterized by the fact that a distance of said ring-shaped electrode from said pointed electrode in direction of the longitudinal axis is smaller or at most the same as a diameter of said ring-shaped electrode.

26. A surgical instrument comprising:
an HF source for producing an HF current;
first and second electrodes connected to said HF source to apply said HF current flowing therebetween to a tissue to be treated, said first and second electrodes being spaced from each other to define a space therebetween; and
an electrically non-conductive spacer received in said space and slidable relative to said first and second electrodes.

27. The surgical instrument defined in claim 26 wherein said spacer has a cutting edge.

* * * * *